United States Patent [19]

Duchesne et al.

[11] Patent Number: 5,684,168
[45] Date of Patent: Nov. 4, 1997

[54] β-PHENYLISOSERINE-(2R,3S), SALTS, PREPARATION AND USE THEREOF

[75] Inventors: Jean-Pierre Duchesne, Lyons; Max Ferraro, Feyzin, both of France

[73] Assignee: Rhone-Poulenc Rorer S.A., Antony, France

[21] Appl. No.: 419,965

[22] Filed: Apr. 10, 1995

Related U.S. Application Data

[63] Continuation of Ser. No. 84,248, filed as PCT/FR92/00032, Jan. 16, 1992 published as WO/922958, Aug. 6, 1992, abandoned.

[30] Foreign Application Priority Data

Jan. 17, 1991 [FR] France ..................... 91 00491

[51] Int. Cl.$^6$ .................. C07D 305/14; C07C 59/48; C07C 229/00
[52] U.S. Cl. .................. 549/510; 549/511; 562/465; 562/470; 562/444
[58] Field of Search .................. 549/510, 511; 562/465, 470, 444

[56] References Cited

U.S. PATENT DOCUMENTS 5,294,737 3/1994 Ojima ..................... 562/444

OTHER PUBLICATIONS

Journal of Organic Chemistry, vol. 56, No. 5, Mar. 1, 1991, pp. 1681–1683, Ojima, et al., Efficient & Practical Asymmetric Sunthesis of the Taxol C-13 Side Chain, N-Benzoyl-(2R,3S)-3-Phenylisoserine, and Its Analogues Via Chiral Ester Enolate-imine Cyclocondensation.

Kamandi et al, "Arch. Pharmazie", vol. 307, pp. 871–878, 1974.

Harada et al, "Bulletin of Chem. Soc. Japan"; vol. 47 (11), pp. 2911–2912, 1974.

Mangatal et al, "Tetrahedron", vol. 45 (13), pp. 4177–4190, 1989.

*Primary Examiner*—Ba K. Trinh
*Attorney, Agent, or Firm*—Finnegan, Henderson, Farabow, Garrett & Dunner, L.L.P.

[57] ABSTRACT

β-phenylisiserine-(2R,3S), salts and preparation thereof through the action of ammonia on β-phenylglycidic-(2R,3R) acid and its use in the preparation of taxane derivatives of general formula:

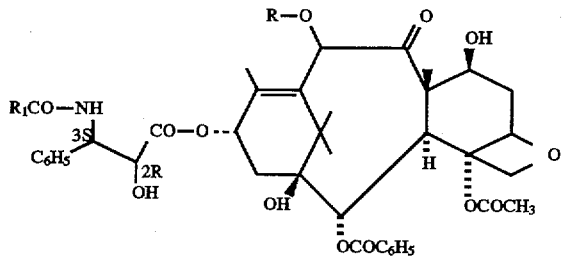

wherein R is hydrogen or —COCH$_3$; and R$_1$ is phenyl or —O—C(CH$_3$)$_3$.

10 Claims, No Drawings

β-PHENYLISOSERINE-(2R,3S), SALTS, PREPARATION AND USE THEREOF

This is a continuation of application Ser. No. 08/084,248, filed on Jul. 7, 1993, now abandoned, which is a 371 application of PCT/FR92/00032 dated Jan. 16, 1992.

The present invention relates to (2R,3S)-β-phenylisoserine of formula:

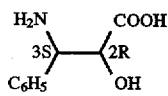

as well as its alkali metal or alkaline earth metal salts and its salts with nitrogenous bases, to its preparation and to its use for the preparation of therapeutically active products.

BACKGROUND OF THE INVENTION

Whereas the (2R,3R), (2S,3S) and (2S,3R) isomers of β-phenylisoserine are known in the scientific literature, e.g. in the papers by E. Kamandi et al., Arch. Pharmaz., 307, 871–878 (1974) by E. Kamandi et al., Arch. Pharmaz., 308, 135–141 (1975) or by K. Harada and Y. Nakajima, Bull. Chem. Soc. Japan, 47, 2911–2912 (1974), (2R,3S)-β-phenylisoserine does not yet appear to have been described other than in ester form [H. Hönig et al., Tetrahedron, 46, (11) 3841–3850 (1990)].

DESCRIPTION OF THE INVENTION

According to the invention, (2R,3S)-β-phenylisoserine, optionally in salt form, may be obtained by the action of ammonia solution on (2R,3R)-β-phenylglycidic acid, preferably in the form of an alkali metal or alkaline earth metal (sodium, potassium, calcium) salt, of an ammonium salt or of a salt with a nitrogenous base (α-methylbenzylamine, pyridine).

Generally, the process is carried out in water, optionally mixed with an organic solvent such as methanol. It is preferable to work in water.

To carry out the process, it is necessary to use an excess of ammonia relative to (2R,3R)-β-phenylglycidic acid. Generally, from 10 to 100 moles of ammonia, and preferably from 50 to 80 moles, are used per mole of (2R,3R)-β-phenylglycidic acid.

The ammonia is preferably used in the form of a concentrated aqueous solution such as a solution whose concentration is between 20 and 32% (w/w) at a temperature in the region of 25° C.

The process being carried out at a temperature of between 0° and 100° C., and preferably between 40° and 60° C. Generally, it is performed at atmospheric pressure or alternatively under an autogenous pressure which is in the region of 2.5 bars at 60° C.

In order to speed up the reaction, it is especially advantageous to work in the presence of an ammonium salt such as ammonium chloride or ammonium hydrogen carbonate. It is preferable to use ammonium hydrogen carbonate which enables the reaction rate to be increased while retaining the selectivity. Generally, a stoichiometric amount of ammonium salt is used relative to the β-phenylglycidic acid employed.

Generally, the process is carried out using the salt of (2R,3R)-β-phenylglycidic acid with α-methylbenzylamine. However, it is also possible to use an alkali metal (sodium, potassium) salt which is obtained by the action of a base (sodium hydroxide, potassium hydroxide) in a stoichiometric amount on the salt of (2R,3R)-β-phenylglycidic acid with α-methylbenzylamine, or the ammonium salt which is obtained by displacement of the salt of (2R,3R)-β-phenylglycidic acid with α-methylbenzylamine by an excess of ammonia solution. In the latter case, it is possible to favor the displacement by continuous or semi-continuous extraction of the α-methylbenzylamine by means of a suitable organic solvent such as toluene.

It is especially advantageous to use the ammonium salt of (2R,3R)-β-phenylglycidic acid, which enables the ring-opening by means of ammonia to be rendered both regioselective and stereoselective.

Irrespective of the manner in which the action of ammonia on (2R,3R)-β-phenylglycidic acid is carried out, the (2R,3S)-β-phenylisoserine may be isolated according to one of the following methods:

1) the excess ammonia may be removed under reduced pressure so as to obtain the ammonium salt of (2R,3S)-β-phenylglycidic acid in aqueous solution. After the addition of a strong mineral acid, the (2R,3S)-β-phenylisoserine precipitates and is separated by filtration, or alternatively 2) before, during or after the removal of the ammonia under reduced pressure, it is possible to add an alkali metal base (sodium hydroxide, potassium hydroxide) or alkaline earth metal base (quicklime or slaked lime); the salt formed precipitates after the addition, where appropriate, of an organic solvent such as acetone. The alkali metal or alkaline earth metal salt thereby obtained is separated by filtration. In order to facilitate salting-out of the salt, especially of the sodium salt, of (2R,3S)-β-phenylisoserine, and to improve the yield, it may be advantageous to saturate the water present in the reaction mixture by adding sodium chloride.

(2R,3R)-β-Phenylglycidic acid may be prepared under the conditions described by J.-N. Denis et al., J. Org. Chem., 51, 46–50 (1986).

In Denis, cis-cinnamyl alcohol, easily obtained from phenylacetylene in 88% yield by hydroxymethylation followed by Lindlar reduction, was subjected to the titanium-catalyzed asymmetric epoxidation process, resulting in a 61–65% yield of the desired (2S,3R)-(−)-phenoxyranemethanol. The phenoxyranemethanol was oxidized by using ruthenium trichloride-sodium periodate. Because of the observed relative instability of the resultant free (2R,3R)-(+)-phenyloxiranecarboxylic acid, the reaction product, without isolation, was routinely converted to the methyl ester with etheral diazomethane.

The (2R,3S)-β-phenylisoserine obtained by carrying out the process according to the invention is especially useful for performing the synthesis of therapeutically active products such as the taxane derivatives of general formula:

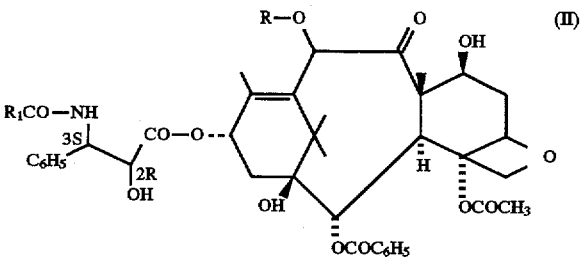

in which R represents a hydrogen atom or an acetyl radical and $R_1$ represents a phenyl or t-butoxy radical.

By the action of a benzoylating agent (benzoyl chloride) or of a t-butoxycarbonylating agent (t-butyl dicarbonate) and then of an agent for protection of the hydroxyl function, β-phenylisoserine yields the product of general formula:

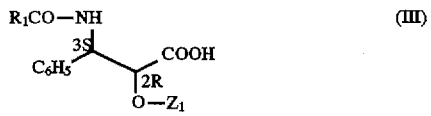

in which $R_1$ represents a phenyl or t-butoxy radical and $Z_1$ represents a group of the hydroxyl function (1-ethoxyethyl).

By condensation of the acid of general formula (III) with baccatine III or 10-deacetylbaccatine III in which the hydroxyl functions at the 7-position and, where appropriate, at the 10-position are protected by protective groups (silyl, 2,2,2-trichloroethoxycarbonyl radicals), followed by replacement of the protective groups with hydrogen atoms, the product of general formula (II) is obtained.

The condensation of the acid of general formula (III) with protected baccatine III or protected 10-deacetylbaccatine III, as well as the replacement of the protective groups with hydrogen atoms, may be carried out under the conditions described in European Patent EP-0,336,840 OR EP-0,336,841.

EXAMPLES

The example which follows, given without implied limitation, shows how the invention may be put into practice.

Example 1

3 kg of α-methylbenzylamine (2R,3R)-β-phenylglycidate, assaying at 98% and the enantiomeric excess of which is greater than 98.5%, and 15 liters of 32% (w/w) ammonia solution are introduced into a column. At the bottom of the column, toluene is introduced by means of a metering pump at a flow rate of 3 to 5 liters/hour. The toluene solution which separates out at the column head is removed by overflowing. After 18 liters of toluene have been introduced, α-methylbenzylamine is no longer detected in the toluene extract.

The ammonium β-phenylglycidate solution obtained above and 30 liters of 32% (w/w) ammonia solution (30 liters) are introduced into a 150-liter autoclave. The autoclave is closed and then heated in the course of 1 hour to 60° C. with stirring. The pressure is in the region of 2.5 bars. Stirring is continued at 60° C. for 5 hours and the autoclave is then allowed to cool to 18° C. The ammonia is removed by distillation under reduced pressure (100–700 mm of mercury; 13.3–93 kPa) at 24° C. after the addition of 9 kg of sodium chloride and 0.42 kg of sodium hydroxide pellets in 2.5 liters of water. When the pressure in the apparatus reaches 45 mm of mercury (6 kPa), the reaction mixture is heated to 48° C. in order to dissolve the salts and is then cooled to a temperature of between −5° and −8° C. for 3 hours.

The white crystals obtained are separated by filtration and then dried at 40° C. under reduced pressure (1 mm of mercury; 0.13 kPa). (2R,3S)-β-Phenylisoserine sodium salt (1932 g), melting point 218° C., is thereby obtained.

The $^{13}C$ nuclear magnetic resonance spectrum of the (2R,3S)-β-phenylisoserine sodium salt, determined in deuterated water at 90 MHz, is characterized by the following chemical shifts (δ): 60.2 ($^{1}JCH=140$ Hz); 80.0 ($^{1}JCH=147$ Hz; $^{2}J=2.6$ Hz); 129.6; 130.2; 131.5; 144.4 and 181.6 ppm.

Example 2

10 kg of α-methylbenzylamine (2R,3R)-β-phenylglycidate (35.08 mol), 15 liters of water and 20 liters of toluene are introduced into a 250-liter reactor, and 10 liters of 4N sodium hydroxide are then added in the course of 10 minutes at a temperature in the region of 20° C. The mixture is stirred for 1 hour. The aqueous phase is separated after settling has taken place. The toluene phase, which contains α-methylbenzylamine, is retained. The aqueous phase is washed with 2 times 10 liters of toluene to remove all of the α-methylbenzylamine. From the combined toluene phases, the α-methylbenzylamine may be isolated.

1.860 kg of ammonium chloride and 162 liters of 20% (w/v) ammonia solution are added to the aqueous phase placed in a 250-liter reactor. The mixture is heated to 50° C. and then kept stirring for 17 hours. After cooling to 35° C., 35 kg of sodium chloride are added and the mixture is then maintained at this temperature for 30 minutes. It is allowed to cool slowly (2 hours) to a temperature of between 0° and 5° C. and is then maintained for 1 hour at this temperature. The precipitate is separated by filtration and then dried under reduced pressure at 50° C. 7 kg of dry product are thereby obtained, which product contains approximately 25% of sodium chloride and approximately 5.300 kg of pure (2R,3S)-β-phenylisoserine sodium salt.

The yield is 72%.

The product thereby obtained may be used in the subsequent synthesis operations without further treatment.

Although the invention has been described in conjunction with specific embodiments, it is evident that many alternatives and variations will be apparent to those skilled in the art in light of the foregoing description. Accordingly, the invention is intended to embrace all of the alternatives and variations that fall within the spirit and scope of the appended claims.

We claim:

1. (2R,3S)-β-Phenylisoserine or a salt thereof selected from alkali metal salts, alkaline earth metal salts and salts with nitrogenous bases.

2. Process for preparing (2R,3S)-β-phenylisoserine, optionally in salt form, comprising reacting ammonia with (2R,3R)-β-phenylglycidic acid or one of its salts, and isolating (2R,3S)-β-phenylisoserine optionally in salt form.

3. Process according to claim 2, wherein from 10 to 100 moles of ammonia are used per mole of (2R,3R)-β-phenylglycidic acid.

4. Process according to claim 1, wherein the reaction is performed in water or in an organic solvent.

5. Process according to claim 4, wherein the solvent is chosen from aliphatic alcohols containing 1 to 4 carbon atoms.

6. Process according to claim 1, wherein the ammonium salt is chosen from ammonium chloride and ammonium hydrogen carbonate.

7. Process according to claim 1, wherein one mole of ammonium salt is used per mole of (2R,3S)-β-phenylglycidic acid employed.

8. Process according to claim 2, wherein the reaction is performed at a temperature of between 0° to 100° C.

9. Method for using the (2R,3S)-β-phenylisoserine according to claim 1 for the preparation of taxanes of formula:

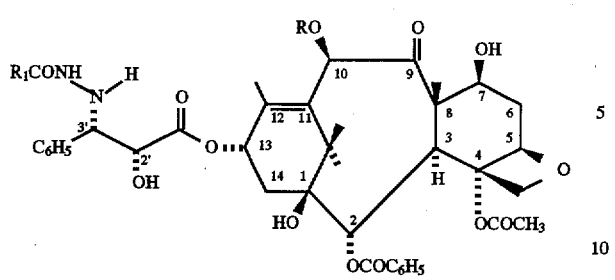

in which R represents a hydrogen atom or an acetyl radical and $R_1$ represents a phenyl or t-butoxy radical, comprising reacting a benzoylating or t-butoxycarbonylating agent and then an agent for protection of the hydroxyl function with (2R,3S)-β-phenylisoserine, condensing the product obtained with baccatine III or 10-deacetylbaccatine III in which the hydroxyl functions at the 7- and, optionally, the 10-positions are protected, and then, after replacing the groups protecting the hydroxyl functions with hydrogen atoms, isolating the product obtained.

10. Process for preparing (2R,3S)-β-phenylisoserine, optionally in salt form, comprising:

reacting ammonia with (2R,3R)-β-phenylglycidic acid or one of its salts at a temperature of between 0° to 100° C.;

said reaction being performed in the presence of an ammonium salt, and with from 10 to 100 moles of ammonia being used per mole of (2R,3R)-β-phenylglycidic acid or one of its salts; and isolating (2R,3S)-β-phenylisoserine optionally in salt form.

* * * * *

UNITED STATES PATENT AND TRADEMARK OFFICE
CERTIFICATE OF CORRECTION

PATENT NO. : 5,684,168
DATED : November 04, 1997
INVENTOR(S) : Jean-Pierre DUCHESNE et al.

It is certified that error appears in the above-identified patent and that said Letters Patent is hereby corrected as shown below:

Claim 7, column 4, lines 60-61, "(2R,3S)-β- phenylglycidic" should read --(2R,3R)-β-phenylglycidic--.

Signed and Sealed this

Fifth Day of January, 1999

Attest:

Attesting Officer

*Acting Commissioner of Patents and Trademarks*